United States Patent [19]

Schrenk et al.

[11] 4,414,332
[45] Nov. 8, 1983

[54] ENDOPROTEINASE-LYS-C AND PROCESS FOR ITS PREPARATION THEREOF

[75] Inventors: Jürgen Schrenk, Weilheim; Peter Wunderwald, Haunshofen, both of Fed. Rep. of Germany

[73] Assignee: Boehringer Mannheim GmbH, Mannheim-Waldhof, Fed. Rep. of Germany

[21] Appl. No.: 297,480

[22] Filed: Aug. 28, 1981

[30] Foreign Application Priority Data

Sep. 10, 1980 [DE] Fed. Rep. of Germany ....... 3034045

[51] Int. Cl.$^3$ ............................ C12N 9/50; C12R 1/01
[52] U.S. Cl. .................................... 435/219; 435/822
[58] Field of Search ......................................... 435/219

[56] References Cited

PUBLICATIONS

Stone et al., Journal of Biological Chemistry, vol. 254, No. 21, pp. 10857–10861, Nov. 10, 1979.

Primary Examiner—Lionel M. Shapiro
Attorney, Agent, or Firm—Felfe & Lynch

[57] ABSTRACT

The present invention provides endoproteinase-Lys-C from bacteria, consisting of a chain of molecular weight 35000 to 38000 Dalton, having a pH optimum at pH 7.7 and being inhibited by aprotinin but not being inhibited by alpha$_2$-macroglobulin, α$_1$-antitrypsin and ethylenediamine-tetraacetic acid.

The present invention also provides a process for obtaining this enzyme, wherein a culture broth of an appropriate bacterial strain which has been filtered or pre-purified by usual methods is chromatographed over carrier-fixed alpha$_2$-macroglobulin-metal complex and the enzyme is obtained from the filtrate.

5 Claims, No Drawings

ENDOPROTEINASE-LYS-C AND PROCESS FOR ITS PREPARATION THEREOF

This invention relates to the endoproteinase-Lys-C, particularly derived from bacteria, to a process for its preparation and to the use thereof.

For various purposes, especially for the hydrolysis of proteins and peptides, for example in the course of sequence determinations, endoproteinases which split proteins or peptides at specific sites are of technical and scientific interest. Thus, an endoproteinase has already been obtained from fungi which hydrolyzes the peptide bond on the amino side of lysine. However, this enzyme is difficult to obtain and, therefore, is not available to a sufficient extent.

An enzyme cleaving proteins at the carboxyl group of lysine has now been found in bacteria which is characterized as endoproteinase-Lys-C and clearly differs in its properties from other bacterial proteases.

The new endoproteinase-Lys-C from bacteria according to the present invention consists of a chain of molecular weight 35000 to 38000 Dalton, has a pH optimum at pH 7.7 and is inhibited by aprotinin but is not inhibited by $\alpha_2$-macroglobulin, $\alpha_1$-antitrypsin and ethylenediaminetetraacetic acid.

The enzyme according to the present invention tends to aggregate under non-reducing conditions, with tetramers with a molecular weight of about 150,000 D and octomers with a molecular weight of about 300,000 D being formed, which are enzymatically active.

As already mentioned, the pH optimum of the new enzyme lies at pH 7.7, determined at 37° C. according to the azocoll method.

In the electrofocussing, the enzyme splits up into numerous bands which extend over almost the whole pH range. This behaviour suggests that the enzyme is a glycoprotein; the isoelectric point of the enzyme cannot, therefore, be determined.

As already indicated, alpha$_2$microglobulin, $\alpha_1$-antitrypsin and ethylenediamine-tetraacetic acid (EDTA, up to $10^{-2}$ M) do not inhibit the enzyme. Benzamidine, on the other hand, inhibits the enzyme about 50% at 2.5 mM and by increasing the benzamidine concentration, 70% inhibition can be achieved. Aprotonin inhibits the enzyme completely.

The following Table 1 shows the substrate specificity of the new enzyme. Its specific activity, measured with tosyl-glycyl-prolyl-lysyl-p-nitroanilide at 25° C., is about 25 U/mg. or about 50 azocoll units/mg. of enzyme at 37° C.

In contradistinction to the known proteinase II from Lysobacter, the enzyme according to the present invention does not hydrolyze the peptide bond at the amino group of lysine but that at the carboxyl group. The small number of bands which appear in the case of gel chromatography of fibrin split products obtained with this enzyme also demonstrate its high specificity.

TABLE 1

| Substrate specificity of endoproteinase Lys-C | |
|---|---|
| substrate | breakdown by endoproteinase Lys-C |
| azocoll | + |
| casein | + |
| fibrinogen | + |
| haemoglobin | + |
| TLME | ++ |
| Chromozym PL ® | ++ |
| S 2251 ® | ++ |
| Tos-Arg-Me | − |
| Chromozym TH ® | − |
| BAEE | − |
| Leu-pNA | − |
| Lys-pNA | − |
| ATEE | − |
| B-chain of insulin | + |

Abbreviations
TLME = tosyl-lysyl methyl ester
BAEE = benzoyl-arginyl ethyl ester
ATEE = arginyl-tyrosyl ethyl ester
Chromozym PL ® = tosyl-glycyl-prolyl-lysyl-p-nitroanilide
Chromozym TH ® = tosyl-glycyl-prolyl-arginyl-p-nitroanilide
S 2251 ® = valyl-leucyl-lysyl-p-nitroanilide The following Table 2 shows the differences of the enzyme according to the present invention from proteases previously found in Lysobacter.

TABLE 2

| enzyme | EC number | molecular weight | reaction mechanism | specificity |
|---|---|---|---|---|
| α-lytic proteinase | 3.4.21.12 | 20,000 D | serine-protease | carboxyl group of neutral amino acids, esp. alanine |
| β-lytic protease | — | 19,000 D | Zn metallo-proteinase | carboxyl group of hydrophobic amino acids, lyse bacterial cell walls |
| AL-1 proteinase I | 3.4.99.29 | 9000 D (gel filtration), 14,000 D (sedimentation equilibrium) | unknown | hydrophobic amino acids, lyse bacterial cell walls (especially gram positive) |
| AL-1 proteinase II | 3.4.99.30 | 17,000 D | unknown | amino group of lysine |
| endoproteinase Lys-C | — | 35–38,000 D (red. SDS gel), about 35,000 D (Sephacryl S-300) | serine-protease | carboxyl group of lysine |

The enzyme according to the present invention can be freed from most impurities from the culture broths of micro-organisms which form this enzyme in sufficient amount, especially from those of the Order Lysobacterales and preferably including those of the Family Lysobacteraceae, for example of the genus Lysobacter (also called Myxobacter), by the usual enzyme purification methods, such as ammonium sulphate fractionation, acetone fractionation and molecular sieve chromatography. The separation of other proteases takes place, according to the present invention, by treatment with carrier-fixed alpha$_2$-microglobulin metal complex. In the case of this process step, which is new for enzyme purification, impurities which are difficult to remove but especially the accompanying proteases, are separated off, whereas the endoproteinase Lys-C according to the present invention remains in solution and can be isolated therefrom, Thus, according to the process of the present invention for obtaining endoproteinase Lys-C, a culture broth of an appropriate bacterial strain which has been filtered or pre-purified by usual methods is chromatographed over carrier-fixed alpha$_2$-macroglobulin-metal complex and the enzyme is obtained from the filtrate.

In the above-mentioned alpha$_2$-macroglobulin-metal complex, the metal is a divalent metal selected from zinc, cobalt, nickel and/or copper. The use of this complex and its preparation is described in more detail in Federal Republic of Germany Patent Application No. P 3034043.3.

As already mentioned, the treatment according to the present invention with carrier-fixed alpha$_2$-macroglobulin-metal complex can be carried out starting directly from the culture broth. However, it is preferable previously to separate off the proteins from other substances and to carry out a pre-fractionation.

Separating off of the proteins from the culture filtrate preferably takes place by precipitation with ammonium sulphate, although other conventional protein precipitation agents which do not impair the enzymatic activity of the active proteins contained therein can also be used. In the case of adding ammonium sulphate, this is preferably added up to a concentration of 2.5–3.5 M and more preferably of 3–3.2 M. The precipitate thereby formed is separated off, for example by filtration, the whole of the desired activity being obtained. After dissolving with water and preferably removal of residual ammonium sulphate by dialysis, the so obtained solution can be subjected either to the alpha$_2$-microglobulin-metal complex chromatography or to a further pre-purification.

If a further pre-purification is desired, then it is preferable to carry out an ammonium sulphate fractionation, the fraction precipitating between 2 and 3 M ammonium sulphate concentration containing the desired activity. In a first step, ammonium sulphate is thereby preferably added to a concentration of 0.7–1.3 M, the precipitate obtained is separated off and the ammonium sulphate concentration is then increased to 3 M and preferably to 2.25–2.32 M. The active precipitate thereby obtained is separated off in the usual way and freed from remaining ammonium sulphate by dialysis.

If the so obtained solution is not subjected to the alpha$_2$-macroglobulin-metal complex treatment, there can also be previously introduced an acetone fractionation and a molecular sieve chromatography. In the case of an acetone fractionation, precipitation is carried out by the addition of 0.3–1.5 volumes and preferably of 0.5–1.2 volumes of acetone, the precipitate is separated off and a further 1.2 volumes of acetone added thereto, whereafter the precipitate is separated off and dissolved in a buffer of pH 7.5–9, the buffer concentration preferably being from 0.01–0.05 M. After dialysis for the removal of residual acetone and possible concentration of the solution obtained, it can be chromatographed over a molecular sieve, for example a cross-linked dextran, such as "Sephadex" G-100, the desired activity being eluted from the column at the beginning, whereas the known AL-1 proteinase I is only eluted towards the end ("Sephadex" is a Registered Trade Mark). The eluate is, optionally after concentration, chromatographed over carrier-fixed alpha$_2$-microglobulin-metal complex, the desired endoproteinase-Lys-C thereby passing through. The elution preferably takes place in the pH range of 7.0–8.5 at a buffer concentration of 0.03–0.08 M. The usual buffer substances effective in this range can be used, tris buffer, hepes buffer and phosphate buffer being preferred. Good results have been achieved at pH 6.5–9 and 0.01–0.1 M buffer concentration. The eluate contains pure endoproteinase-Lys-C and buffer and can be directly lyophilised.

The new enzyme according to the present invention is especially useful for the sequence determination of proteins and peptides. Due to its high specificity, it can also be used therapeutically, for example in cases of coagulation disturbance or other diseases in which the splitting of protein chains is desired.

The following Examples are given for the purpose of illustrating the present invention:

EXAMPLE 1

Obtaining endoproteinase-Lys-C from *Lysobacter enzymogenes ssp. enzymogenes DSM* 1895 (ATCC 27796)

Starting material: 206 liters of Lysobacter culture filtrate.

206 Liters of Lysobacter culture filtrate are slowly precipitated out with solid ammonium sulphate to 3–3.2 M. The slight flocculent precipitate is filtered off. The precipitate on the filter is dissolved with a little distilled water, precipitated out with solid ammonium sulphate to 0.9 M (1.3 to 3 M) and centrifuged. The supernatant is again precipitated out to 2.25 to 2.32 M ammonium sulphate and the precipitate filtered or centrifuged off, dissolved in about 400 ml. distilled water and dialysed against running tap water.

The dialysate is mixed with 0.5 to 1.2 volume of acetone at −20° C. and centrifuged off. The clear supernatant is now mixed with a further 1.2 volumes (calculated from the initial volume) of acetone, the precipitate is centrifuged off and dissolved as concentrated as possible with 0.025 M tris buffer (pH 9) and dialysed against 10 liters of the same buffer.

The dialysate is applied to a "Sephadex" G-100 column with the following dimensions: diameter 5 cm.; length 150 cm.; column volume about 2.9 liters.

The column is equilibrated with 0.025 M tris buffer (pH 9.0) and, after application of the dialysate, is subsequently washed with the same buffer. Lysobacter protease is eluted at the beginning.

The eluate is precipitated out with solid ammonium sulphate to 3.2 M and centrifuged. The precipitate, taken up concentrated, is dialysed against 0.05 M tris buffer (pH 8.0).

Alpha$_2$-macroglobulin-Zn complex, covalently bound to agarose, is employed for the further purification. 100 ml. of this carrier material are packed into a 3 cm. diameter column of 17.5 cm. length and washed with 0.05 M tris buffer (pH 8.0) until no protein is present in the wash.

The dialysate is now applied to the column and subsequently washed with 0.05 M tris buffer (pH 8.0). Proteinase-Lys-C passes through.

The flow-through is dialysed against 0.05 M glycine (pH 8.0) and diluted to 0.4 mg./ml. with the same buffer and lyophilised.

Total yield:
about 50–140 mg. protein
6–23 U/mg. proteinase Lys-C
Chromozym TH activity <0.2%

EXAMPLE 2

Determination of endoproteinase Lys-C

Preparation of the solutions:

1. 0.025 M tris, 0.001 M EDTA, pH 7.7

0.303 g. tris and 37.2 mg. EDTA are dissolved in about 80 ml. double distilled water and adjusted with 2 N hydrochloric acid to pH 7.7 and made up to 100 ml.

2. Chromozym-PL (14 μM/ml.)

9 mg. Chromozym-PL are dissolved in 1 ml. double distilled water.

3. Endoproteinase-Lys-C solution

Dissolve 10 mg. of lyophilisate in 1 ml. double distilled water. Before use, it is diluted 1:100 with Solution 1.

Carrying out:
405 nm 1 cm. semi-microcuvette
25° C. test volume 1.07 ml.

Pipette into the cuvette:

| | |
|---|---|
| Solution 1 | 1 ml. |
| Solution 2 | 0.05 ml. |
| mix, warm for about 2 minutes at 25° C. | |
| sample solution 3 | 0.02 ml. |
| mix, | |
| from the linear phase, calculate ΔE/min. after about 5 minutes. | |

Calculation:

$$\frac{\Delta E/min. \times 1.07}{10.4 \times 0.02} \times 100 = U/ml. \text{ endoproteinase-Lys-C}$$

It will be understood that the specification and examples are illustrative but not limitative of the present invention and that other embodiments within the spirit and scope of the invention will suggest themselves to those skilled in the art.

What is claimed is:

1. Endoproteinase-Lys-C from Lysobacterales which cleaves proteins at the carboxyl group of lysine and consists of a chain of molecular weight 35000 to 38000 Dalton, having a pH optimum at pH 7.7 and inhibited by aprotinin but not inhibited by $\alpha_2$-macroglobulin, $\alpha_1$-antitrypsin and ethylenediamine-tetraacetic acid.

2. Process for obtaining endoproteinase-Lys-C as claimed in claim 1, which comprises chromatographing a culture broth of an endoproteinase-Lys-C producing strain of Lysobacterales which has been filtered or pre-purified by convention methods over carrier-fixed $\alpha_2$-microglobulin-metal complex, and obtaining said enzyme from the filtrate.

3. Process as claimed in claim 2, wherein the chromatographing is carried out in 0.01–0.1 M buffer, pH 6.5–9.

4. Process as claimed in claim 2, wherein the protein is precipitated from the filtered culture broth by means of ammonium sulphate, the precipitate is fractionated, after again dissolving, between 1.3 and 3 M ammonium sulphate and the fraction which is insoluble in this range is dissolved in water and, after dialysis, fractionated with acetone between 1.2 and 2.4 vol. of acetone.

5. Process as claimed in claim 4, wherein, after dissolving, the precipitate of the acetone fractionation is fractionated over a molecular sieve and the protein fractions eluted at the beginning of the chromatography subjected to the $\alpha_2$-macroglobulin-metal complex chromatography.

* * * * *

UNITED STATES PATENT AND TRADEMARK OFFICE
CERTIFICATE OF CORRECTION

PATENT NO. : 4,414,332
DATED : November 8, 1983
INVENTOR(S) : Schrenk et al.

It is certified that error appears in the above-identified patent and that said Letters Patent is hereby corrected as shown below:

| | |
|---|---|
| Col. 1, line 40 | "microglobulin" should be -- macroglobulin --. |
| Col. 2, line 62 | "microglobulin" should be -- macroglobulin --. |
| Col. 3, line 31 | "microglobulin" should be -- macroglobulin --. |
| Col. 3, line 64 | "microglobulin" should be -- macroglobulin --. |
| Claim 2, line 6 | "microglobulin" should be -- macroglobulin --. |

Signed and Sealed this

Eighteenth Day of December 1984

[SEAL]

Attest:

Attesting Officer

GERALD J. MOSSINGHOFF

Commissioner of Patents and Trademarks